June 24, 1975 D. L. ARMSTRONG Plant Pat. 3,733
NECTARINE TREE
Filed Feb. 7, 1974
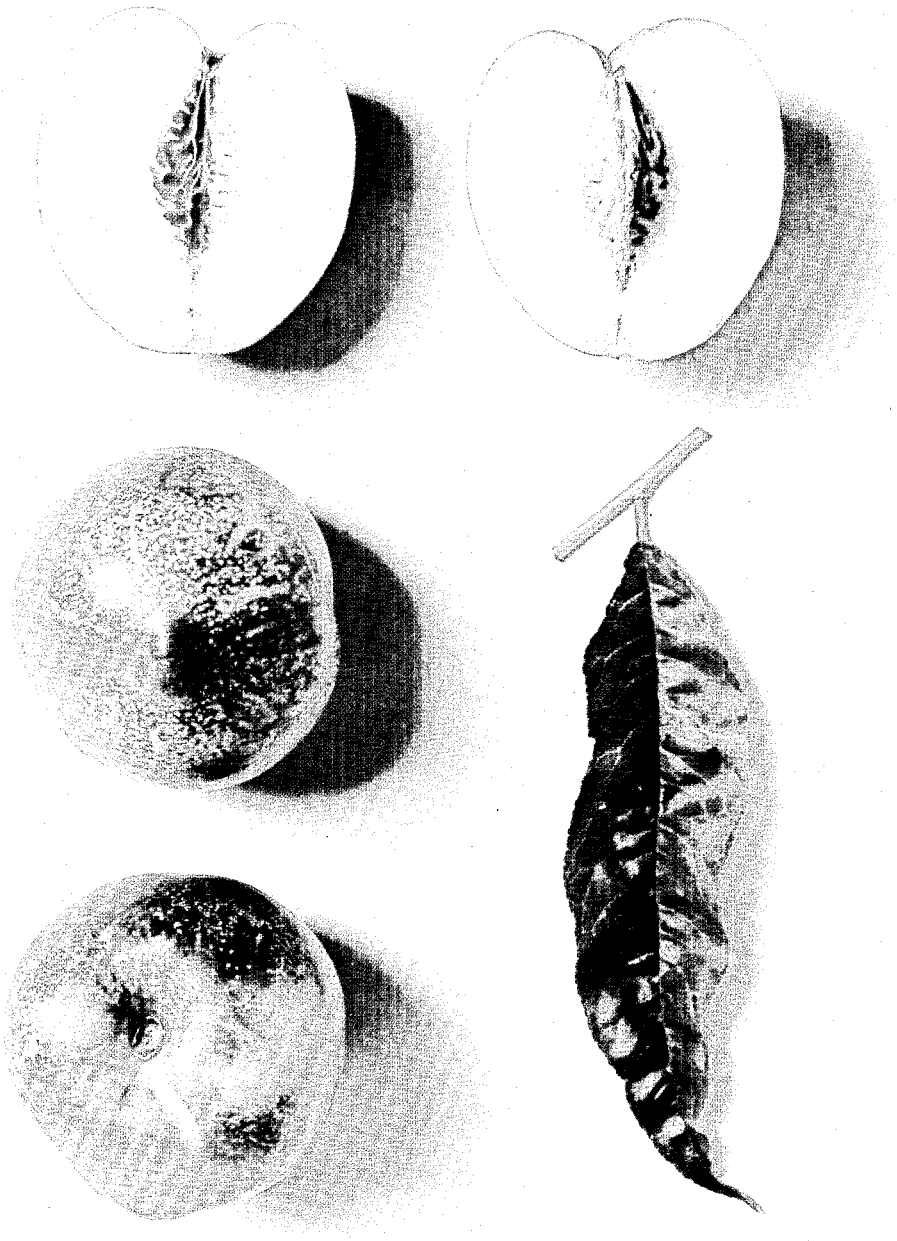

United States Patent

Plant Pat. 3,733
Patented June 24, 1975

3,733

NECTARINE TREE

David L. Armstrong, Orange, Calif., assignor to Armstrong Nurseries, Inc., Ontario, Calif.

Filed Feb. 7, 1974, Ser. No. 440,480
Int. Cl. A01h 5/03
U.S. Cl. Plt.—40 1 Claim

ABSTRACT OF THE DISCLOSURE

A new variety of nectarine tree, manifesting a vigorous upright habit of growth, with dense foliage tending to assume the form of a vase. The variety is a regular bearer, and very productive. The fruit is of the freestone type, having white melting flesh which is very juicy and flavorful, as well as highly aromatic. The fruit ripens early, usually from June 12 to June 22, and the size is large in comparison to the size of other early-ripening varieties. It withstands storage and shipping unusually well. Chilling requirements are comparable to those of the Springtime peach, in Wasco, Calif.

This invention relates to the discovery of a new variety of nectarine tree, which was first asexually reproduced by David L. Armstrong, in Wasco, Calif. It produces freestone fruits which ripen rather early, from about the 12th of June to the 22nd of that month, and which have excellent storage and shipping properties.

The variety was originally propagated through open-pollination of an unnamed, undisseminated peach seedling, which was heterozygous both for white and yellow flesh and for peach and nectarine. In its ancestry was the nectarine Pioneer. The purpose in the pollination was to obtain large, freestone nectarines. The properties of the new variety will be reproduced through successive propagations by budding.

Comparison of the new cultivar and other white fleshed nectarines presently on the market shows that Silver Lode, for example, ripens in late June and early July, and is sweet in flavor, while the new cultivar has a richer balance between sweet and acid and ripens earlier. Incidentally, Silver Lode displays more red in the skin, whereas the new cultivar is more mottled. Sequoia ripens in mid-August, two months later than the new variety. Hayes Late ripens even later, namely about Sept. 1. It is a clingstone variety, whereas the new cultivar is of the freestone type. Morton is a semiclingstone nectarine with showy flowers. The new variety is a freestone, and its flowers are not showy.

The new cultivar differed from its open-pollinated seed parent in several ways. Most notably, the parent was a peach whereas the new cultivar is a nectarine. The seed parent had yellow fleshed fruit, whereas the new cultivar is white fleshed. The fruit of the seed parent ripened generally in early to mid-August, in the neighborhood of Wasco, Calif., where the tree now being described was propagated. The fruit of the new cultivar ripens much earlier, namely in mid-June.

The tree is vigorous and upright in its habit of growth. It bears regularly, and is highly productive. The foliage displays reinform glands, and the bloom is non-showy. The blossoms are small, single, and star-shaped. They are deep pink in color, and they appear in late February and early March, in Wasco, Calif. Chilling requirements in that location are comparable to those of the Springtime peach.

Throughout this specification, color names beginning with a small letter signify that the name of that color, as used in common speech, is aptly descriptive. Color names with capital letters designate values based upon the Nickerson Color Fan, put out by Munsell Color Co.

The accompanying drawing shows a characteristic leaf, full views from opposite ends of the fruit, and one fruit cut at right angles to the suture, showing in one, half the stone in place, and in the other, the stone cavity.

The fruit ripens at about mid-June, with first picking possibly on June 12, and the last picking ten days later. The fruit, in addition to its highly aromatic, juicy and flavorful flesh, manifests unusually good keeping and shipping qualities. It holds up well in storage, compared to other varieties of nectarines generally, and particularly to varieties of early-ripening types.

The *tree* is of medium size, of upright habit, and vase-formed as to its overall appearance. It is hardy in Wasco, Calif.

The *trunk* is of medium size, having bark of medium texture, neither very smooth nor very shaggy.

The *branches* are of medium size, and the bark, like that of the trunk, is of medium character, and somewhat glossy. Its color is between Moderate Reddish Brown, 7.5R3/6, and Moderate Reddish Brown, 10R3/4. The lenticels are of moderate number, and of medium size.

The *leaves* of this new variety are from 5½" to 6¾" long, and 1½" to 1⅞" wide; they are acuminate, or lanceolate in shape, of medium thickness and smooth. Their color on the upper side is between Moderate Yellow Green, 5GY5/6, and Moderate Olive Green, 5GY4/3. On the under side, their color value lies between Moderate Olive Green, 7.5GY4/4, and Moderate Yellow Green, 5GY5/6.

The leaf margin is glandular and finely serrate. The petiole is of medium length and medium thickness. There are usually from two to four glands, although sometimes five. They are reniform, and positioned on the margin of the leaf just above the petiole and on the petiole near the attachment of the leaf blade. Their color is near Strong Yellow Green, 2.5GY7/10. The stipules are short and early deciduous.

The *flower* buds are half-hardy, medium in size and length, conic and somewhat appressed to free.

The flowers first bloom, usually about Feb. 25 in Wasco, Calif. They attain full bloom, usually about Mar. 16. This is a medium bloom period, compared with other varieties. The flowers are small, single, and deep pink in color. They are non-showy.

The *fruit*, as now described, was eaten firm and ripje the 30th day of June. The fruit at that stage was large and uniform in size, having an axial diameter of 3" and a transverse diameter, in the plane of the suture, of from 2½" to 2⅝". At right angles to the suture plane, the measurement was 2⅜" to 2¾", thus indicating a uniform, fairly symmetrical, but slightly oblong shape.

The suture was deep near the base of the fruit, becoming shallow one-third to one-half way from the base to the apex; extending beyond the apex over the entire circumference as an inconspicuous line, with a slight depression beyond the pistil point. The ventural surface was rounded, with slightly unequal lips toward the base. The stem cavity was rounded, except that it was usually elongated in the plane of the suture, with the suture showing on one side. The depth of the cavity was ¼", and its width 5/16". The base of the fruit was slightly rounded to truncate, and its apex short and rounded to slightly truncate, with a short apical pistil point.

The stem was ⅜" long, of medium caliper and glabrous. It adheres with medium strength to the stone.

The skin, which was medium thick and of medium toughness, clung tenaciously to the flesh, with little if any tendency to crack. Its color varied from Brilliant Yellow Green, 2.5GY8/9, to Brilliant Yellow Green, 2.5GY9/8, blushed heavily with from Deep Pink, 2.5R6/11, to Dark Red, 2.5R3/7. There was no down, which is a characteristic of nectarines.

The color of the flesh was betwen off-white and Brilliant Greenish Yellow, 7.5Y9/8, with some very small areas of the pit cavity being colored near Strong Red, 5R4/12. The amygdalin was scant, the juice abundant. The texture was firm, fine and melting; the fibers few and tender. The flesh ripens relatively evenly, but earliest at the apex along both lips. The flavor was distinct yet mild, and the aroma was pronounced and distinct. The eating quality of the fruit is considered from good to best.

The *stone* was free, and parts from the flesh smoothly. It is large, being about 1¾″ long, 1⅛″ in breadth, and ¾″ thick. The form is ovoid, but cuneate toward the apex; the hilum oval to oblong; the apex acuminate. The sides of the stone are slightly unequal, with a somewhat flattened curve on both sides. The surface of the sides is irregularly furrowed toward the apex, and pitted toward the base. The ridges are rounded toward the apex.

The pits were both circular and elongated, having a ventral edge which is of medium thickness, with wing toward the base. The dorsal edge is medium, with deep narrow grooves throughout, and interrupted ridges on either side. The color of the stone, when first exposed, is between Moderate Orange Yellow, 7.5YR8/8, and Strong Orange Yellow, 7.5YR7/11, with some small areas of near Dark Reddish Orange, 7.5R4/11, on the edges and at the apex. The stone had no tendency to split.

The fruits are well adapted for market use, shipping, and as a dessert. It has good keeping quality, and good rseistance to insects and diseases, as compared with other cultivars now in trade. It has good shipping quality.

I claim:

1. A new variety of asexually reproduced nectarine tree, substantially as herein illustrated and described, said tree being characterized in particular by its tendency to produce fruit which ripens in mid-June in a growing region such as Wasco, Calif., in which locale the chilling requirement is comparble to that of the Springtime peach, the said fruit, when mature, being about three inches in axial diameter, of the freestone type, white fleshed, juicy, aromatic, and full-flavored; the fruit of said new variety being further characterized by excellent storing and shipping characteristics.

No references cited.

ROBERT E. BAGWILL, Primary Examiner

UNITED STATES PATENT OFFICE

CERTIFICATE OF CORRECTION

Patent No. PP-3733 Dated June 24, 1975

Inventor(s) David L. Armstrong

It is certified that error appears in the above-identified patent and that said Letters Patent are hereby corrected as shown below:

Column 1, line 61, "reinform" should be --reniform--.

Column 2, line 2 , "one, half" should be --one half--.

Column 2, line 44, "ripje" should be --ripe--.

Column 2, line 55, "ventural" should be --ventral--.

Column 2, line 64, "was" should be --is--.

Column 3, line 10, "was" should be --is--.

Column 4, line 4, "fruits are" should be --fruit is--.

Signed and Sealed this second Day of December 1975

[SEAL]

Attest:

RUTH C. MASON
*Attesting Officer*

C. MARSHALL DANN
*Commissioner of Patents and Trademarks*